United States Patent
Drake et al.

(10) Patent No.: US 9,937,322 B2
(45) Date of Patent: Apr. 10, 2018

(54) ASSEMBLIES AND METHODS FOR DEFLECTABLE SHAFT CATHETERS

(71) Applicant: Medtronic, Inc., Minneapolis, MN (US)

(72) Inventors: Ronald A Drake, St. Louis Park, MN (US); Lester O Stener, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 187 days.

(21) Appl. No.: 14/694,579

(22) Filed: Apr. 23, 2015

(65) Prior Publication Data

US 2016/0310700 A1    Oct. 27, 2016

(51) Int. Cl.

| | | |
|---|---|---|
| A61M 31/00 | (2006.01) |
| A61M 25/01 | (2006.01) |
| A61M 25/00 | (2006.01) |
| A61M 39/22 | (2006.01) |

(52) U.S. Cl.
CPC .... *A61M 25/0136* (2013.01); *A61M 25/0014* (2013.01); *A61M 25/0097* (2013.01); *A61M 25/0133* (2013.01); *A61M 25/0147* (2013.01); *A61M 39/22* (2013.01); *A61M 2205/0216* (2013.01)

(58) Field of Classification Search
CPC ..................... A61M 25/0136; A61M 25/0147
See application file for complete search history.

(56) References Cited

U.S. PATENT DOCUMENTS

| | | |
|---|---|---|
| 4,233,734 A | 11/1980 | Bies |
| 4,322,885 A | 4/1982 | Osada |
| 5,666,970 A | 9/1997 | Smith |
| 5,702,373 A | 12/1997 | Samson |
| 6,599,296 B1 | 7/2003 | Gillick et al. |
| 7,419,477 B2 | 9/2008 | Simpson et al. |

(Continued)

FOREIGN PATENT DOCUMENTS

| | | |
|---|---|---|
| EP | 0254701 | 1/1988 |
| EP | 1726326 A2 | 11/2006 |
| EP | 2465568 A1 | 6/2012 |

OTHER PUBLICATIONS (PCT/US2016/025807) PCT Notification of Transmittal of the International Search Report and the Written Opinion of the International Searching Authority, dated Jul. 1, 2016, 13 pages.

*Primary Examiner* — Emily Schmidt

(57) ABSTRACT

A catheter assembly includes a pull wire and a control member subassembly, wherein the pull wire is secured to a post of the subassembly that may extend through a slot of a handle, and an engagement feature of the subassembly, being supported by an elastically deformable support of the subassembly resting on a railway of the handle, confronts a mating feature of the handle to interlock therewith, responsive to the support being un-deformed. The post, engagement feature, and support may be integrally formed together in a single-piece component, wherein the engagement feature may be one or two rows of teeth formed in a surface of an upper portion of the component, and the support may be a pair of flexible cantilever beam members of a lower portion of the component. Furthermore, the mating surface and railway may be integrally formed in an inner surface of a shell of the handle.

24 Claims, 10 Drawing Sheets

(56) References Cited

U.S. PATENT DOCUMENTS

| | | |
|---|---|---|
| 7,497,853 B2 | 3/2009 | Fischer et al. |
| 7,678,074 B2 | 3/2010 | Fischer et al. |
| 7,993,384 B2 | 8/2011 | Wu et al. |
| 8,177,773 B2 | 5/2012 | Ovcharchyn et al. |
| 8,206,343 B2 | 6/2012 | Racz |
| 8,676,290 B2 | 3/2014 | Tegg |
| 8,706,260 B2 | 4/2014 | Stewart et al. |
| 8,721,587 B2 | 5/2014 | Berthiaume et al. |
| 8,784,468 B2 | 7/2014 | Gerdts et al. |
| 8,790,386 B2 | 7/2014 | Dwork |
| 8,911,487 B2 | 12/2014 | Bennett et al. |
| 8,920,432 B2 | 12/2014 | Drake et al. |
| 8,926,588 B2 | 1/2015 | Berthiaume et al. |
| 9,526,522 B2 | 12/2016 | Wood et al. |
| 2006/0264819 A1* | 11/2006 | Fischer ............ A61M 25/0136 604/95.04 |
| 2012/0158021 A1* | 6/2012 | Morrill ............ A61M 25/0136 606/139 |
| 2012/0323254 A1 | 12/2012 | Bonde et al. |
| 2013/0012925 A1 | 1/2013 | Berthiaume et al. |
| 2013/0079798 A1 | 3/2013 | Tran et al. |
| 2013/0103047 A1 | 4/2013 | Steingisser et al. |
| 2013/0131667 A1 | 5/2013 | Jenson et al. |
| 2013/0131693 A1 | 5/2013 | Berthiaume et al. |
| 2014/0228800 A1 | 8/2014 | Rezac et al. |
| 2014/0243844 A1 | 8/2014 | Clancy et al. |
| 2014/0336456 A1 | 11/2014 | Demers et al. |
| 2015/0246205 A1 | 9/2015 | Schaeffer |

* cited by examiner

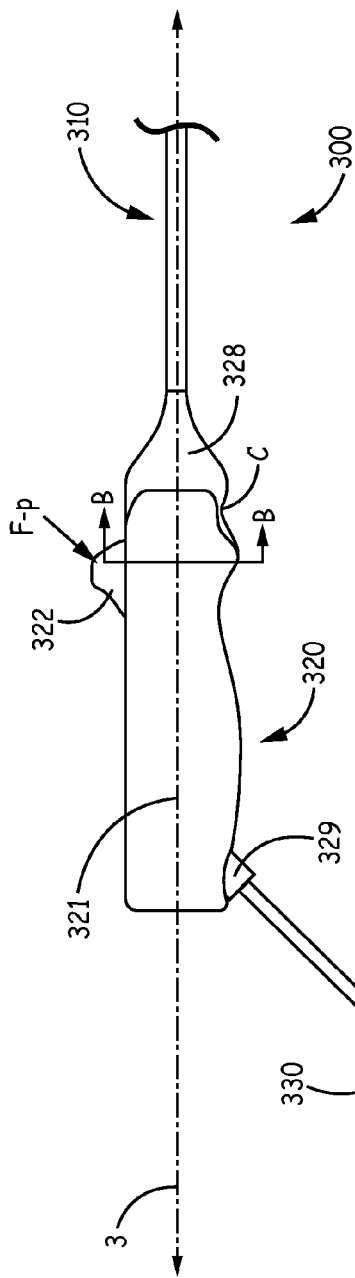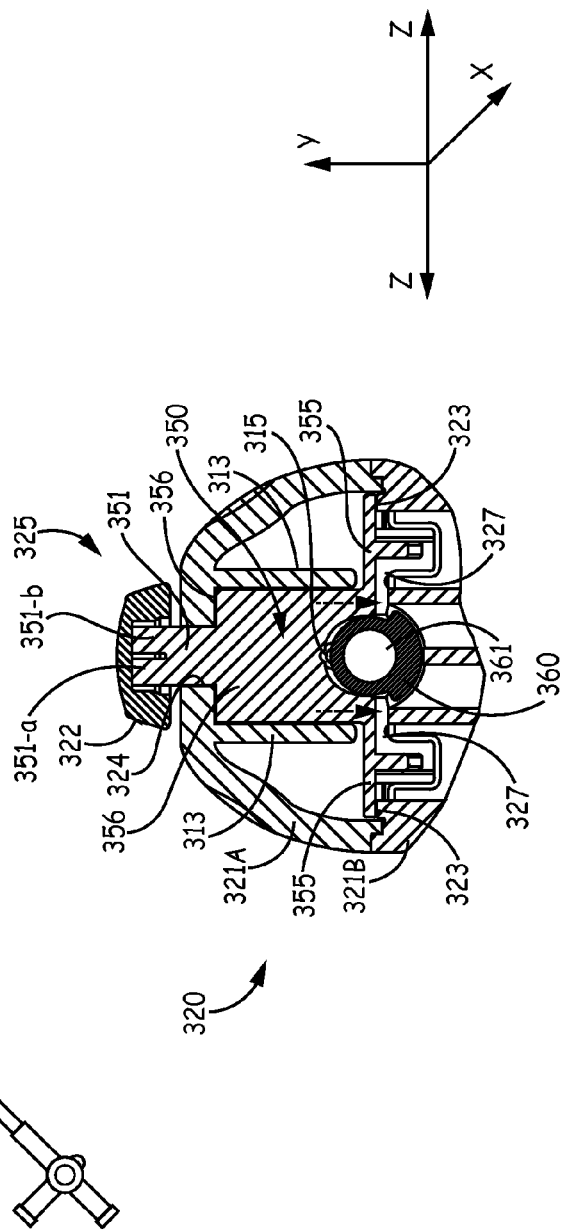

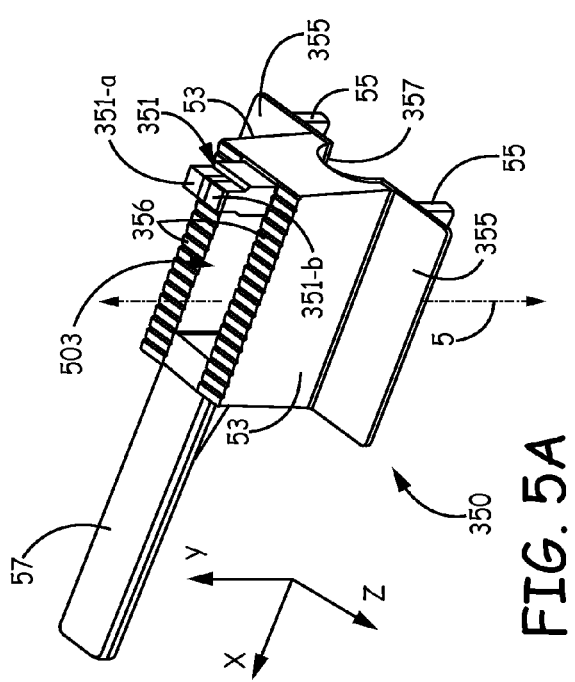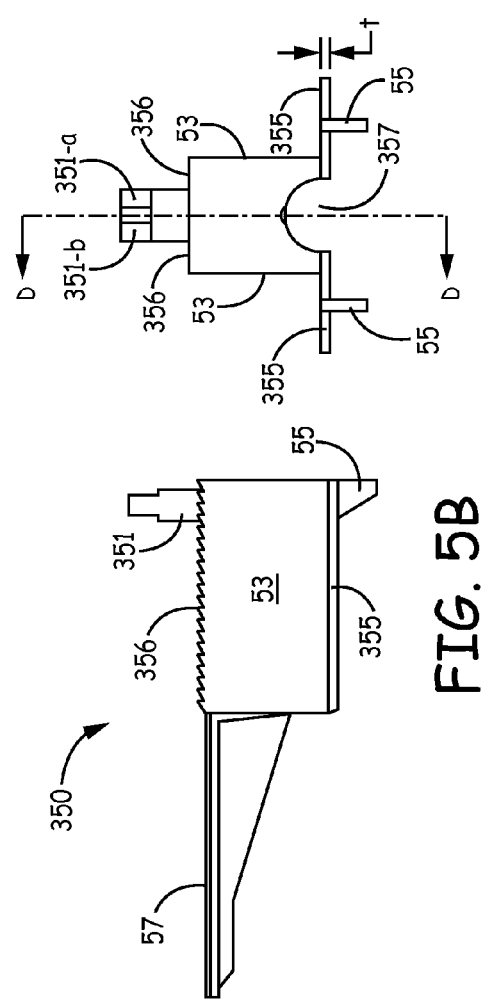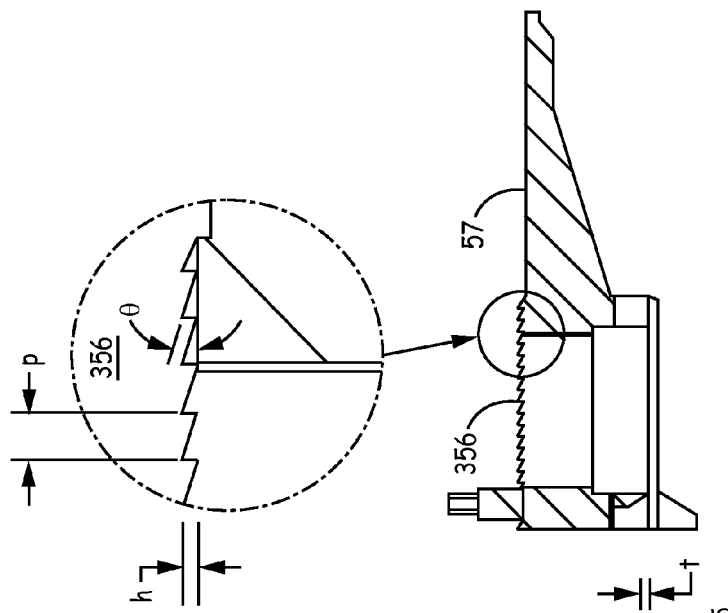
FIG. 5A
FIG. 5B
FIG. 5C
FIG. 5D

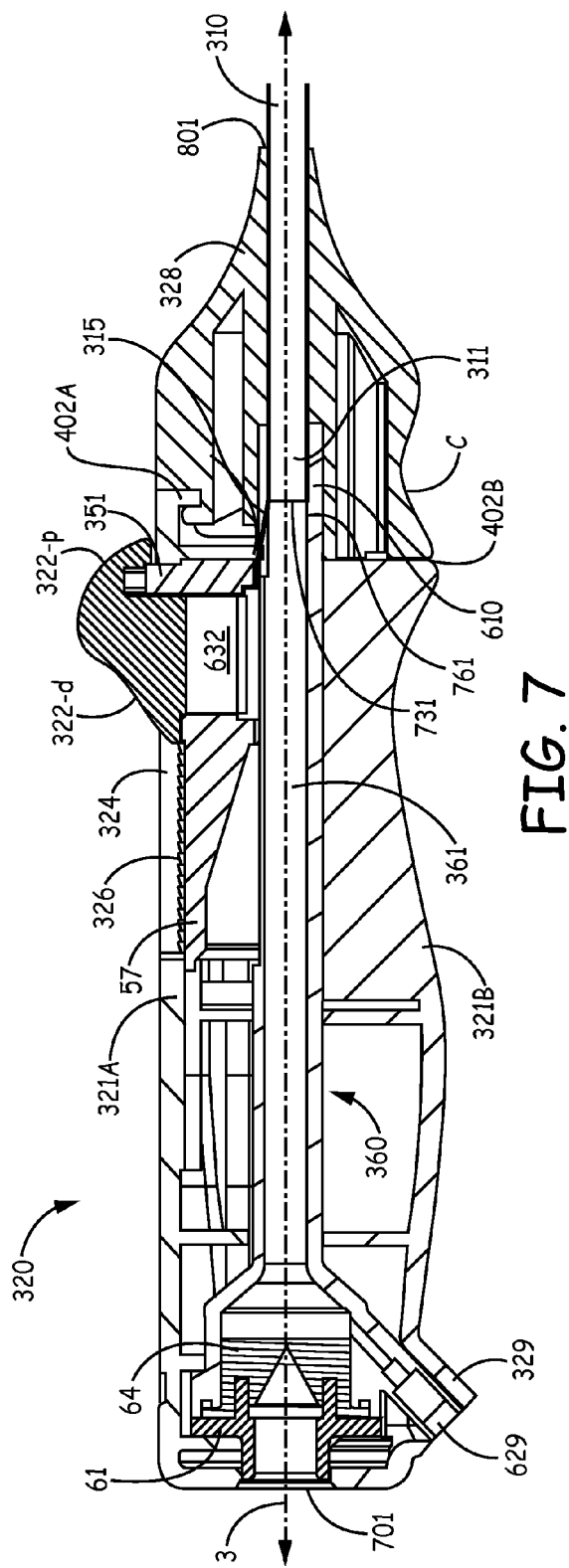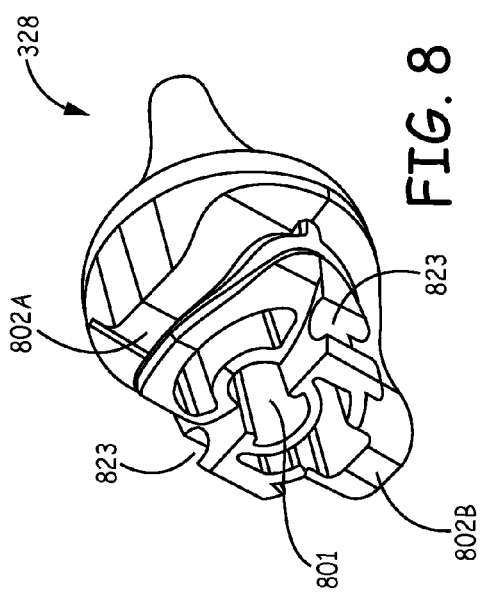

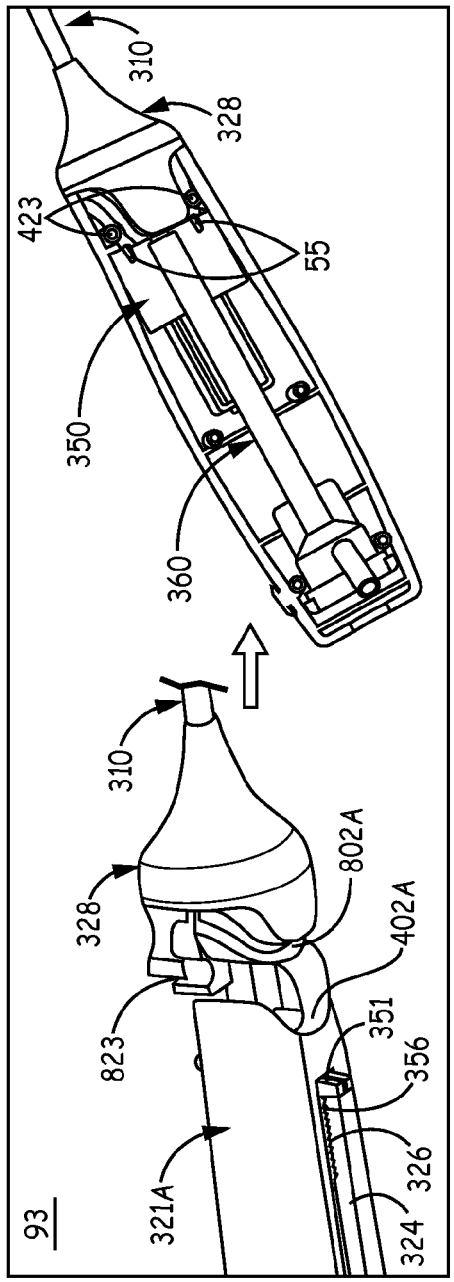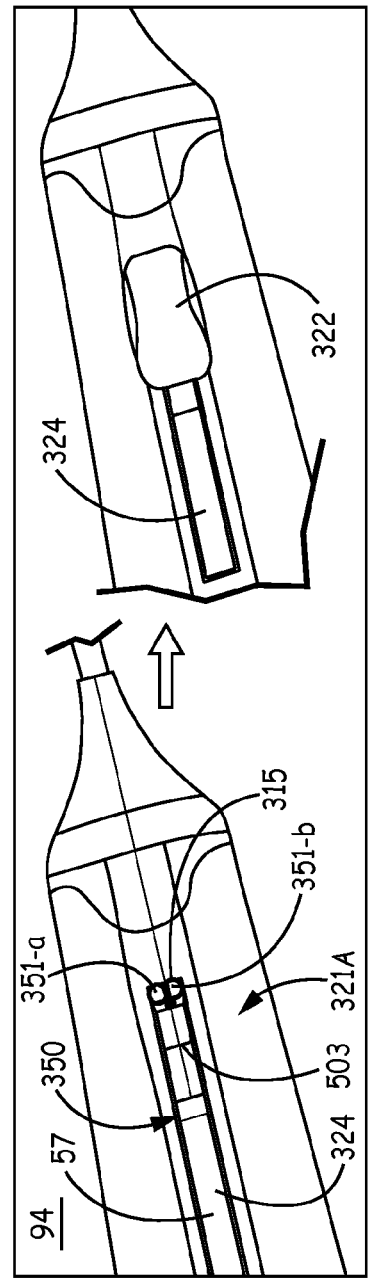

ASSEMBLIES AND METHODS FOR DEFLECTABLE SHAFT CATHETERS

CROSS-REFERENCE TO RELATED APPLICATION

The present application is related to the co-pending and commonly assigned U.S. Patent Application having the Ser. No. 62/151,771, and entitled INTERVENTIONAL MEDICAL SYSTEMS AND ASSEMBLIES THEREOF, which is filed concurrently herewith, and incorporated by reference herein.

FIELD OF THE DISCLOSURE

The present invention pertains to deflectable shaft catheters, and more particularly to assemblies thereof and associated construction methods.

BACKGROUND

Those skilled in the art of interventional medicine are familiar with various types of deflectable shaft catheters used to deliver medical therapy and/or provide medical monitoring. In many cases, a shaft of such a catheter has a pull wire extending along a length thereof, wherein a distal end of the pull wire is anchored to the shaft at a location just distal to a deflectable segment of the shaft. A proximal end of the pull wire is typically secured to a control member subassembly of the catheter, for example, being mounted in a handle of the catheter and including an operator interface. Thus, an operator, when grasping the catheter handle, can actuate the pull wire by applying a force to the operator interface, thereby deflecting the catheter shaft to maneuver a distal portion of the shaft toward a target site within a body of a patient. Although a variety of assemblies suitable for deflectable shaft catheters are known in the art, there is still a need for new assemblies that can enhance operator functionality while having a relatively simple construction.

SUMMARY

According to some embodiments of the present invention, a deflection assembly for a deflectable shaft catheter includes a pull wire and a control member subassembly that may be mounted in a handle of the assembly, wherein a proximal end of the pull wire is secured to a post of the subassembly, for example, which extends through an elongate slot of a shell of the handle; and wherein an engagement feature of the subassembly, which is supported by an elastically deformable support of the subassembly resting on a railway of the handle, confronts a mating feature of the handle for interlocking engagement therewith, responsive to the elastically deformable support being un-deformed. The interlocking engagement prevents the control member subassembly from moving along a length of the handle slot, but responsive to the operator applying a particular force vector to an operator interface of the control member subassembly, which may be coupled to the post, the elastically deformable support deforms against the railway of the handle so that the engagement feature of the control member subassembly moves out from the interlocking engagement with the mating feature of the handle, and the control member subassembly moves along the length of the handle slot.

In some preferred embodiments, to simplify the construction of the above-described deflection assembly, for example, by reducing a number of parts, the post, engagement feature, and elastically deformable support of the control member subassembly are all integrally formed together in a single-piece slider component having an upper portion and a lower portion, wherein the engagement feature may be formed in a surface of the upper portion, out from which the post protrudes, and the elastically deformable support may be a pair of opposing flexible cantilever beam members of the lower portion. Furthermore, the mating surface and railway of the handle are preferably integrally formed in an inner surface of the handle shell. According to some construction methods for the deflection assembly, the slider component is mounted within a first portion of the handle shell so that a post of the slider component extends through the slot, and so that the engagement surface of the slider component confronts the mating feature of the shell first portion for interlocking engagement therewith; and a proximal end of a pull wire, for example, that extends out from a proximal opening of a lumen of the shaft, may be inserted through an aperture of the mounted slider component, from the lower portion to the upper portion thereof, and then secured to the post of the mounted slider component. After securing the pull wire proximal end, a second portion of the handle shell, which includes the railway formed in the inner surface thereof, is attached to the first portion of the handle shell so that the elastically deformable support of the mounted slider component rests against the railway.

According to some embodiments and methods, the deflection assembly includes a hub, which is coupled to a proximal end of the catheter shaft and then mounted in the first portion of the handle shell, so that the mounted slider component is in sliding engagement therewith, prior to attaching the second portion of the handle shell to the first portion. The hub may be bonded to the proximal end of the shaft, in some embodiments, or, in some alternate embodiments, the hub is over-molded onto the proximal end of the catheter shaft and includes an aperture formed therethrough, and through which the pull wire passes, responsive to the pull wire proximal end extending through the aperture of the slider component. In the latter case, the proximal opening of the lumen of the catheter shaft from which the pull wire extends, to pass through the aperture of the hub, defines a proximal, terminal end of the shaft.

BRIEF DESCRIPTION OF THE DRAWINGS

The following drawings are illustrative of particular embodiments of the present invention and therefore do not limit the scope of the invention. The drawings may or may not be to scale, and are intended for use in conjunction with the explanations in the following detailed description. Embodiments will hereinafter be described in conjunction with the appended drawings wherein like numerals denote like elements, and:

FIG. 3A is an elevation view of a proximal portion of a deflectable shaft catheter, according to some embodiments;

FIG. 3B is a cross-section view through section line B-B of FIG. 3A, according to some embodiments;

FIG. 5A is a perspective view of a slider component of a control member subassembly, according to some embodiments;

FIG. 5B is an elevation view of the slider component, according to some embodiments;

FIG. 5C is an end view of the slider component, according to some embodiments;

FIG. 5D is a cross-section view through section line D-D of FIG. 5C, according to some embodiments;

FIG. 7 is a longitudinal cross-section view of a deflection assembly, according to some embodiments;

FIG. 8 is a perspective view of a strain relief element that may be employed in conjunction with the deflection assembly in a deflectable shaft catheter, according to some embodiments; and FIGS. 9A-D are schematics outlining some methods for assembling a deflection assembly for a catheter, such as the catheter shown in FIG. 3A.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
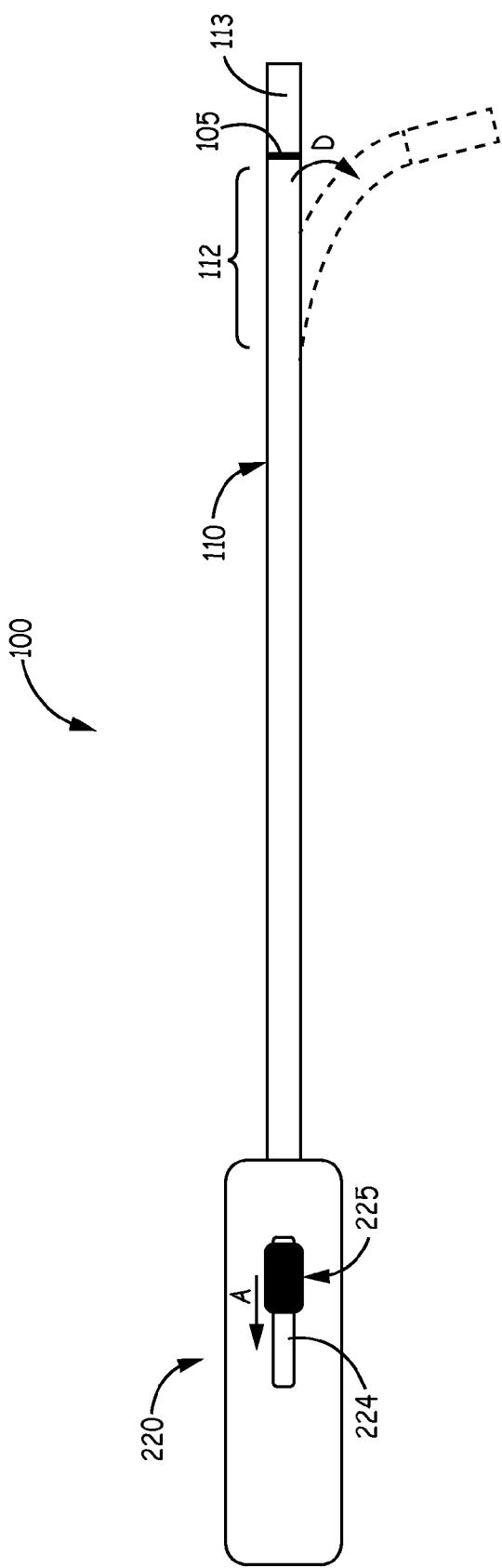
FIG. 1 is a plan view of an exemplary deflectable shaft catheter, according to some embodiments.
Figure 2:
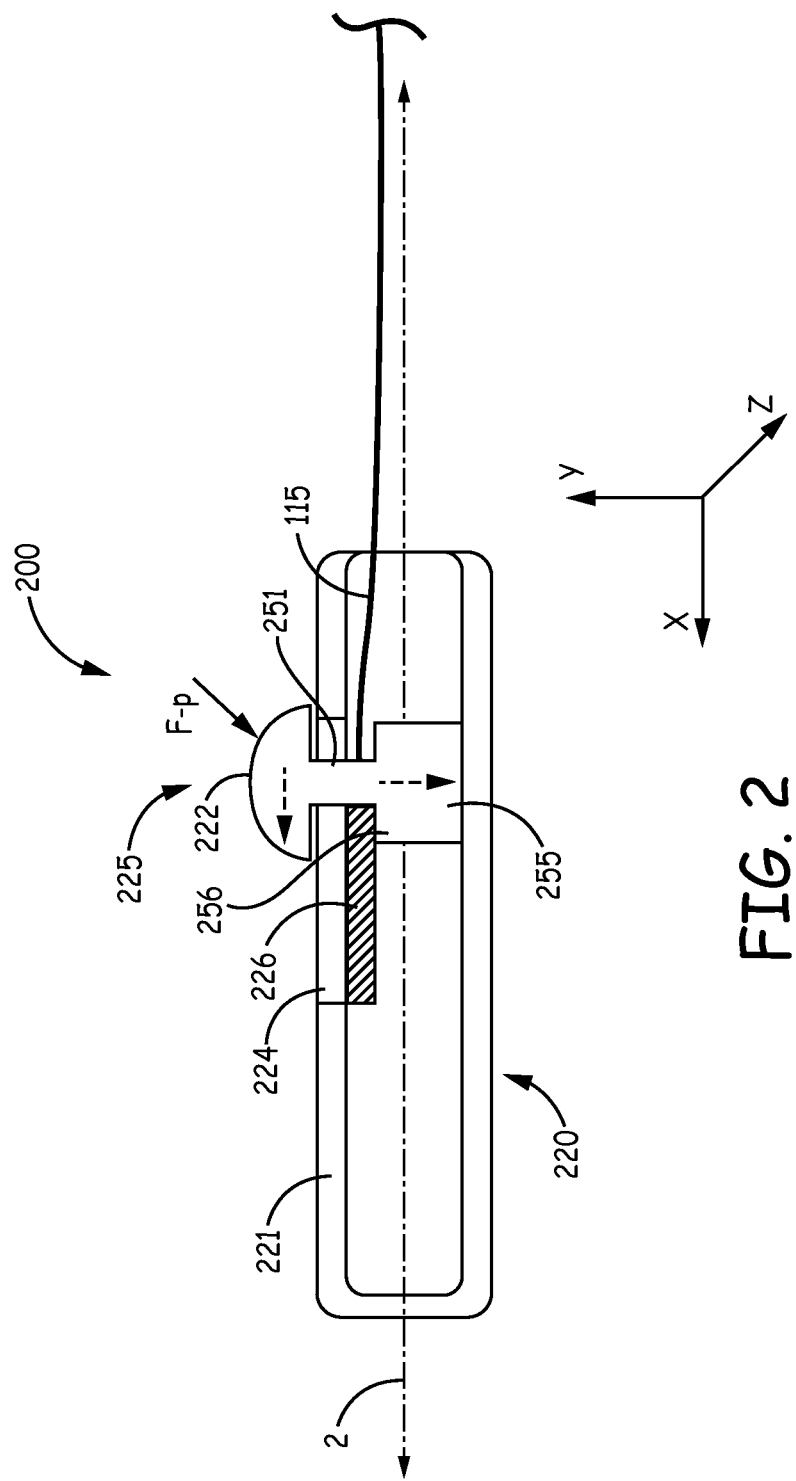
FIG. 2 is a schematic representation of a portion of a deflection assembly, according to some embodiments.

FIG. 1 is a plan view of an exemplary deflectable shaft catheter 100, according to some embodiments. FIG. 1 illustrates catheter including an elongate deflectable shaft 110 and a handle 220 coupled to a proximal end of shaft 110. A deflectable segment 112 of shaft 110 is shown located in proximity to a distal end 113 of shaft; and, according to the illustrated embodiment, a control member subassembly 225 that, responsive to moved in the general direction of arrow A, causes segment 112 of shaft 110 to deflect, per arrow D, for example, via a pull wire 115 (shown in FIG. 2) that extends within a lumen (not shown) of shaft 110 and has a distal end secured to an anchor band 105, just distal to segment 112. FIG. 2 is a schematic representation of a portion of a shaft deflection assembly 200 for catheter 100, which is useful for defining a frame of reference for the configuration and function of control member subassembly 225 in terms of an orthogonal coordinate system of X, Y, and Z axes. FIG. 2 illustrates a proximal end of pull wire 115 secured to a post 251 of subassembly 225 that extends through a slot 224 of a shell 221 of handle 220, and an operator interface 222 coupled to post 251 and located adjacent an outer surface of handle shell 221. Post 251 is shown extending in a vertical direction, generally along the Y axis, which is approximately orthogonal to a length of slot 224 and to a longitudinal axis 2 of handle 220, both extending generally along the X axis.

FIG. 2 further illustrates a force vector F-p, for example, applied by an operator to interface 222 in order to move control member subassembly 225 in a proximal direction along the length of slot 224, which activates pull wire 115 to deflect shaft 110 (FIG. 1). The force vector F-p is shown having a vertical component along the Y axis and a longitudinal component along the X axis (dashed-line arrows). FIG. 2 also schematically depicts an engagement feature 256 of control member subassembly 225, and a mating feature 226 of handle shell 221, which extends alongside slot 224, wherein engagement feature 256, being supported by an elastically deformable support 255 of subassembly 225, confronts mating feature 226 for interlocking engagement therewith. The vertical component of the illustrated force vector F-p deforms support 255 so that engagement feature 256 moves vertically away from mating feature 226, and out of interlocking engagement therewith, to allow movement in a proximal direction in response to the longitudinal component of the force vector F-p; and, responsive to support 255 being un-deformed, either before the force vector F-p is applied, or after the force vector F-p is released, engagement feature 256 interlocks with mating feature 226 to prevent longitudinal movement of control member subassembly 225 in either direction along the length of handle slot 224. Thus, control member subassembly 225 allows the operator to "pull a curve" in deflectable shaft 110 with pull wire 115 (dashed lines in FIG. 1), by moving subassembly 225 proximally, and then allows the operator to release the force vector F-p while control member subassembly 225 still maintains the curve, since, upon release of the force vector F-p, support 255 elastically returns to the un-deformed state, at which engagement feature 256 and mating feature 226 interlock.

FIG. 3A is an elevation view of a proximal portion of a deflectable shaft catheter 300, according to some embodiments, which includes a shaft deflection assembly configured for operation in a similar fashion to the schematic description of FIG. 2. FIG. 3A illustrates catheter 300 including a deflectable shaft 310 that extends through a strain relief element 328 and is coupled to a handle 320 of the shaft deflection assembly. FIG. 3A further illustrates handle 320 extending along a longitudinal axis 3, and catheter 300 further including a flushing assembly 330, which is connected to a side port 329 of handle 320, and an operator interface 322 of a control member subassembly 325, more of which can be seen in the cross-section view of FIG. 3B. The force vector F-p shown in FIG. 3A, which is similar to that described above, may be applied by a thumb of an operator whose hand grasps around handle 320, for example, with forefingers contacting strain relief element 328 along a surface C thereof. Deflectable shaft 310 may be constructed according to the description of a deflectable shaft disclosed in the above-referenced, commonly assigned and application (Ser. No. 62/151,771), according to some embodiments.

Figure 4A:
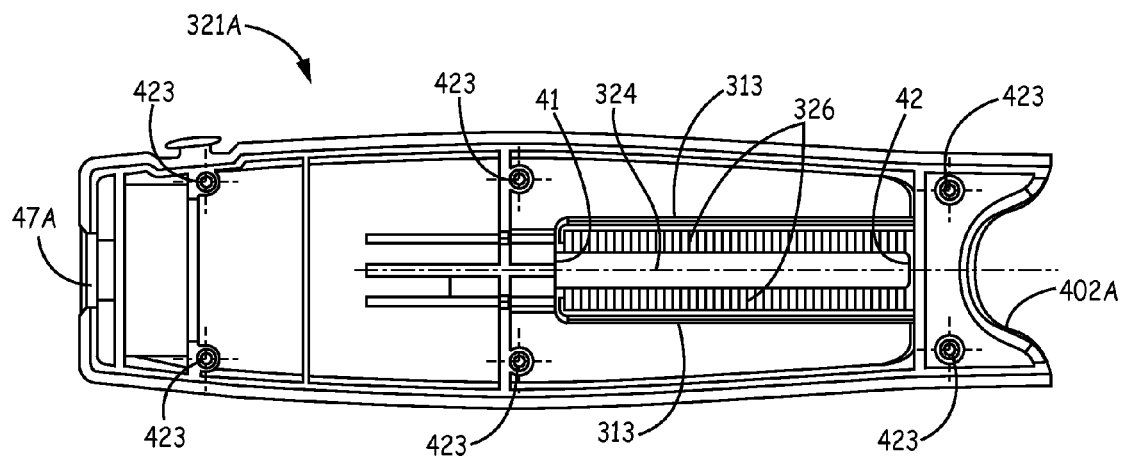
FIGS. 4A-B are plan views of an inner surface of a handle shell, according to some embodiments.
Figure 4B:
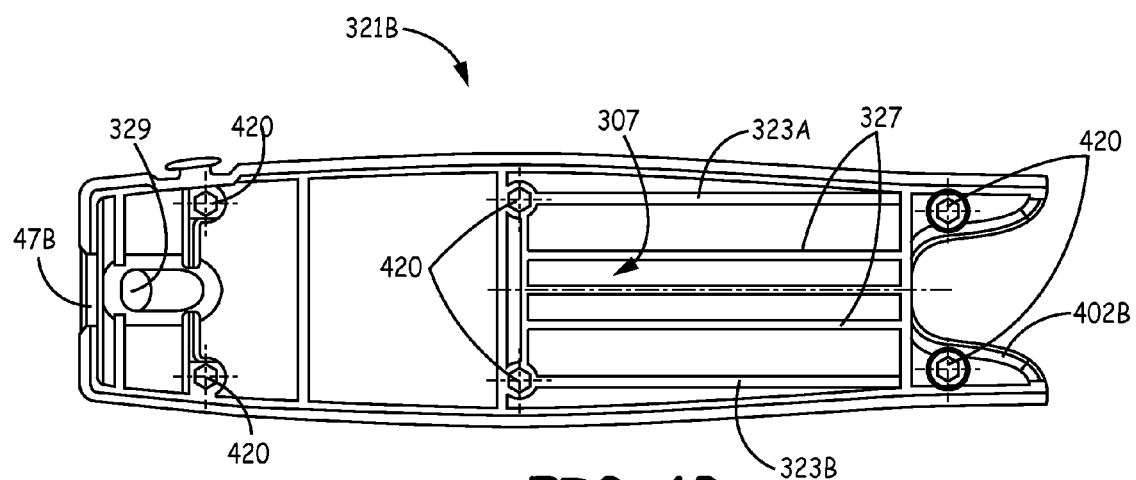

With reference to FIG. 3B, handle 320 may be formed by a shell 321 that surrounds a majority of subassembly 325, wherein shell 321 is preferably divided into a first portion 321A and a second portion 321B, plan views of which are shown in FIGS. 4A-B, respectively. FIG. 3B includes the X, Y, Z orthogonal coordinate system (with X axis coming out from the page and corresponding to longitudinal axis 3 of FIG. 3A), to serve as a frame of reference for control member subassembly 325. FIG. 3B illustrates operator interface 322 being in the form of a button member that is secured to a post 351 of subassembly 325. A pull wire 315 of subassembly 325 is secured to post 351, as will be described in greater detail below, and post 351, which is shown being located between first and second engagement features 356 of control member subassembly 325, extends vertically, along the Y axis and through a slot 324 of handle 320. According to the illustrated embodiment, each engagement feature 356 of subassembly 325 confronts a corresponding mating feature of handle shell 321, which may be, for example, a row of teeth 326 formed in inner surface of shell 321 on either side of slot 324, as shown in FIG. 4A. FIG. 3B further illustrates a pair of opposing cantilever beam members 355, which extend generally along the Z axis and form an elastically deformable support of control member subassembly 325. According to some preferred embodiments, post 351, engagement features 356, and the elastically deformable support/beam members 355 are all integrally formed together in a single-piece slider component 350, which will be described in greater detail below, in conjunction with FIGS. 5A-D.

FIG. 3B shows cantilever beam members 355 resting on a railway 323 that protrudes out from the inner surface of handle shell 321; and FIG. 4B illustrates railway 323 being formed by longitudinally extending first and second rails 323A, 323B, each of which supports a corresponding beam member 355, wherein rails 323A, 323B are preferably integrally formed in the inner surface of shell second portion 321B. With further reference to FIG. 3B, beam members 355 bend in response to the vertical component (shown with dashed-line arrows) of the force vector F-p applied to operator interface 322 (FIG. 3A), so that engagement features 356 move out from interlocking engagement with the mating feature of handle (e.g., rows of teeth 326 on either side of slot 324, shown in FIG. 4A), thereby freeing subassembly 325 to move proximally, in response to the longitudinal component of the force vector F-p, along a length of slot 324, which is defined, along the X axis, between a proximal end 41 thereof and a distal end 42 thereof (FIG. 4A). The bending of beam members 355 may be limited by a stop member 327 that protrudes from the inner surface of handle shell 321. FIGS. 3B and 4B illustrate stop member 327, preferably integrally formed in the inner surface of shell second portion 321B, being located in between rails 323A and 323B.

FIGS. 4A-B further illustrate the inner surface of handle shell first portion 321A including a plurality of pin members 423 protruding therefrom, and the inner surface of handle shell second portion 321B including a corresponding plurality of receptacles 420 formed therein, which are configured to receive pin members 423 in a press fit so that perimeter edges of each shell portion 321A, 321B come together in confronting engagement, for example as illustrated in FIG. 3B. With further reference to FIGS. 4A-B, in conjunction with FIG. 3A, a distal edge 402A, 402B of each shell portion 321A, 321B, respectively, is configured to interface with strain relief element 328, as described in greater detail below. According to some exemplary embodiments, handle shell portions 321A, 321B are injection molded from a relatively rigid medical grade plastic, such as Acrylonitrile butadiene styrene (ABS), according to methods known in the art.

FIG. 5A is a perspective view of single-piece slider component 350 of control member subassembly 325, according to some embodiments; and FIGS. 5B-D are elevation, end, and cross-section views of component 350, according to some embodiments. FIG. 5A shows a vertical axis 5 of component 350, which generally corresponds to the Y axis of the orthogonal coordinate system serving as the frame of reference for control member subassembly 325. Along vertical axis 5, upper and lower portions of component 350 are defined. FIGS. 5A-C illustrate the upper portion of component 350 including first and second engagement features 356 and post 351, and the lower portion of component 350 including elastically deformable support/cantilever beam members 355. With reference to FIG. 5C, according to an exemplary embodiment, a thickness t of each cantilever beam member 355 is approximately 0.040 inch; and, in some preferred embodiments, component 350 is injection molded from a medical grade, living-hinge type plastic known to those skilled in the art, for example, nylon, which enhances the above-described elastically deformable support function of beam members 355. FIGS. 5A-D further illustrate the upper portion of slider component 350 including a tail portion 57, and the lower portion of slider component 350 including bumper features 55, both of which are described below in the context of the deflection assembly.

FIGS. 5A and 5C further illustrate component 350 including opposing sidewalls 53, which extend along vertical axis 5 and between the upper and lower portions, and between which an aperture 503 extends, also along axis 5 and between the upper and lower portions. With reference back to FIGS. 3B and 4A, slider component 350 is mounted in first portion 321A of handle shell 321 such that each sidewall 53 thereof is adjacent to a corresponding sidewall 313 of first portion 321A. According to the illustrated embodiment, aperture 503 of slider component 350 allows passage of a proximal end of pull wire 315 (FIG. 3B) therethrough, from shaft 310 (FIG. 3A), for securing pull wire 315 to post 351. According to FIGS. 3B, 5A and 5C, post 351 preferably includes a pair of pillars 351-a, 351-b extending side-by-side along vertical axis 5, so that the proximal end of wire 315 may be wrapped around and in between pillars 351-a, 351-b, for example, as described below in conjunction with FIGS. 6 and 9C. Furthermore, in control member subassembly 325, operator interface/button member 322 may be fitted within aperture 503 of component 350, for example, as described below in conjunction with FIGS. 6 and 7.

Figure 6:
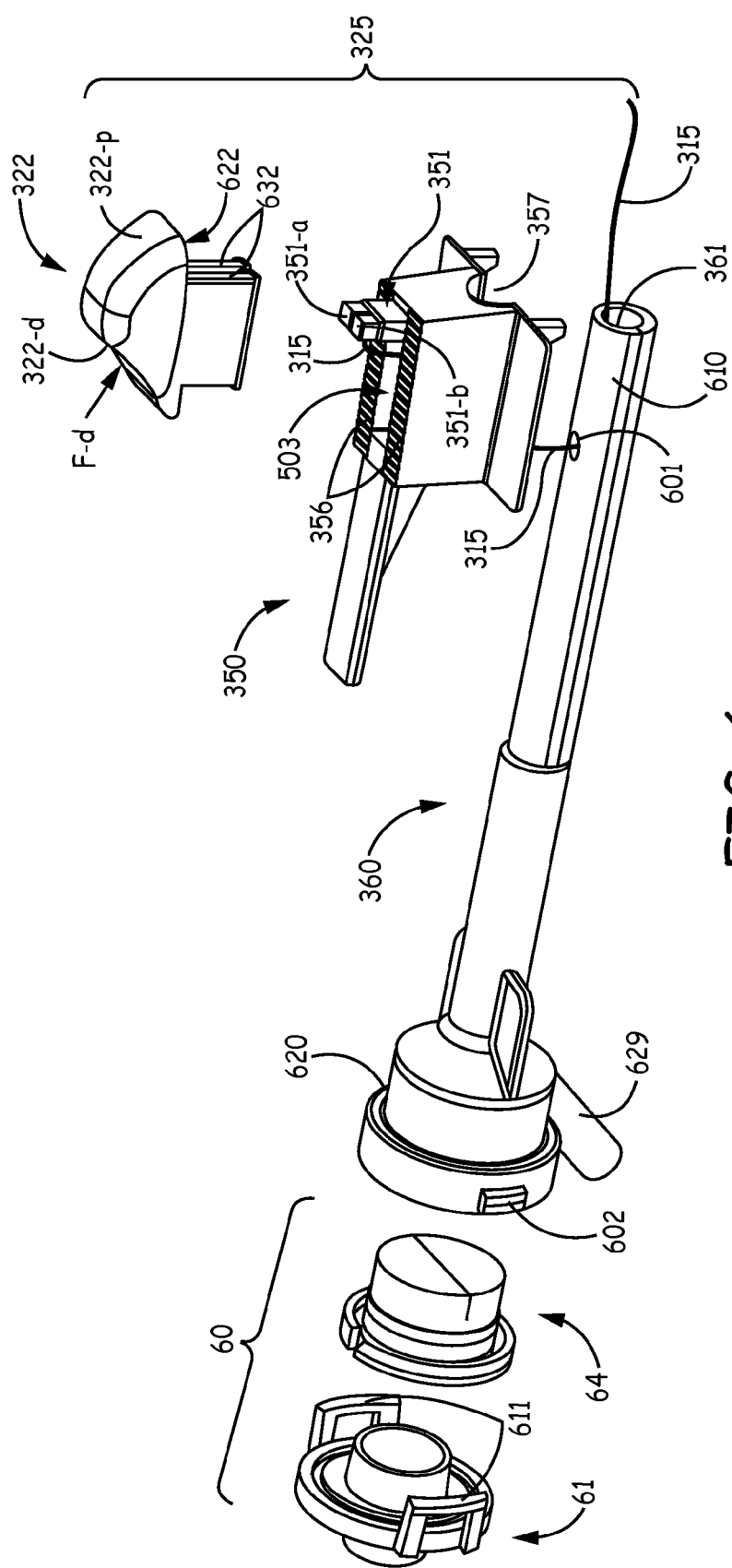
FIG. 6 is an exploded perspective view of a portion of a deflection assembly, according to some embodiments.

FIGS. 5A, 5C and 5D further illustrate the lower portion of slider component 350 including an open channel 357 that extends longitudinally between cantilever beam members 355 and is sized to receive catheter shaft 310, or, preferably, a hub 360 of the deflection assembly, as seen in FIG. 3B and further illustrated in the context of the deflection assembly in FIG. 6. According to an exemplary embodiment, hub 360 is formed from a relatively rigid medical grade plastic, for example, polypropylene or polyether block amide. With reference to FIGS. 3B and 6, according to some embodiments, an inner surface of a tubular sidewall of hub 360 defines a lumen 361 that is in fluid communication with a lumen of catheter shaft 310 (FIG. 3A), wherein a distal end 610 of the tubular sidewall of hub 360 (FIG. 6) may be coupled to a proximal end 311 of shaft 310, for example, as described below in conjunction with FIGS. 7 and 9A. According to the illustrated embodiment, hub 360 rests on inner surface of second portion 321B of handle shell 321, in a space 307 (FIG. 4B) between protrusions of stop member 327; and control member subassembly 325 is slideably engaged with the tubular sidewall of hub 360, via open channel 357, for movement along the length of slot 324 in response to the longitudinal component of the above-described force vector F-p.

FIGS. 5A, 5B, and 5D further illustrate each of engagement features 356 defined by a longitudinally extending row of teeth formed in a surface of the upper portion of single-piece slider component 350, for example, over a length of approximately 0.91 inch, to interlock with the corresponding row of teeth 326 of handle 320 (FIG. 4A) responsive to component 350 being mounted within handle shell 321, as described above. With reference to the enlarged detail view of FIG. 5D, according to an exemplary embodiment, a pitch p of each row of teeth is approximately 0.050 inch, a height h of each tooth is approximately 0.016 inch, and an angle θ of each tooth is approximately 18 degrees.

FIG. 6 is an exploded perspective view of a portion of the deflection assembly for catheter 300 (FIG. 3A), according to some embodiments. FIG. 6 shows the lower portion of slider component 350 positioned in proximity to distal end 610 of the tubular sidewall of hub 360 for mounting in sliding engagement therewith (e.g., with the tubular sidewall received in open channel 357), and operator interface/button member 322 positioned in proximity to the upper portion of slider component 350 to be fitted together therewith. Button member 322 is shown having a first operator interface surface 322-*p*, which is oriented to receive application of the above-described force vector F-p that moves control member subassembly 325 in a proximal direction, to 'pull a curve' in deflectable shaft 310 (FIG. 3A), and a second operator interface surface 322-*d*, which is oriented to receive the application of another force vector F-d that has a similar vertical component as that of force vector F, but has a longitudinal component oriented in the opposite direction to move subassembly 325 distally, and thereby straighten deflectable shaft 310. FIG. 6 further illustrates the proximal end of pull wire 315 extending through an aperture 601 of the tubular sidewall of hub 360, according to some embodiments, and through aperture 503 of component 350, and wrapped around and in between pillars 351-*a*, 351-*b* of post 351. According to the illustrated embodiment, and with reference to the longitudinal cross-section view of FIG. 7, legs 632 of button member 322 are configured for a snap fit within aperture 503 so that a cavity 622 of button member 322, which is located beneath surface 322-*p*, is press fit around pillars 351-*a*, 351-*b*, thereby securing pull wire 315 to component 350.

FIG. 6 illustrates hub 360 including another sidewall extending laterally from a proximal end 620 of the aforementioned tubular sidewall to define a side port 629 of hub 360 that, with reference to FIG. 7, extends within the above-referenced side port 329 of handle 320 (FIGS. 3A and 4B). Hub side port 629 provides a means for connecting flushing assembly 330 to handle 320, as described in greater detail below, and, with further reference to FIG. 7, hub side port 629 is in fluid communication with hub lumen 361. FIGS. 6 and 7 further illustrate hub 360 including a valve subassembly 60 that attaches to a proximal opening of hub lumen 361, the proximal opening being defined by proximal end 620 of the tubular sidewall. Valve subassembly 60 is shown including a valve member 64 and a valve cap 61 configured to secure valve member 64 within the proximal opening of hub lumen 361. According to an exemplary embodiment, valve member 64 may formed from medical grade silicone rubber in a slit valve configuration known in the art, which is sized for a press fit within the proximal opening of hub lumen 361. FIG. 6 further illustrates valve cap 61 including a pair of flap members 611, each configured for interlocking with a corresponding laterally protruding feature 602 of hub 360, for example, as shown in FIG. 9D. With reference to FIG. 7, responsive to hub 360 being assembled within handle shell 321, valve subassembly 60 is fitted within a proximal opening 701 thereof, according to some embodiments. With reference back to FIGS. 4A-B, proximal opening 701 of handle shell 321 may be formed by opposing proximal edges 47A, 47B of first and second portions 321A, 321B, respectively, of handle shell 321.

FIG. 7 further illustrates proximal end 311 of deflectable shaft 310, which extends through a lumen 801 of strain relief element 328, being inserted within the distal opening of hub lumen 361 for coupling to distal end 610 of hub 360. According to the illustrated embodiment, the inner surface of the tubular sidewall of hub 360 includes a shoulder 761 formed therein and against which a proximal, terminal end 731 of shaft 310 abuts. In some preferred embodiments, the proximal end of pull wire 315 exits from a lumen of shaft 310 at proximal, terminal end 731 to extend through aperture 601 of hub 360, as shown in FIG. 6. But according to some alternate embodiments, shaft 310 may include an opening into s pull wire lumen of shaft 310 is located distal to proximal, terminal end 731, so that pull wire 315 exits the lumen just distal to distal end 610 of hub 360.

FIG. 8 is a perspective view of strain relief element 328, according to some embodiments. FIG. 8 illustrates strain relief element 328 having an upper edge 802A configured for interlocking with distal edge 402A of shell portion 321A, and a lower edge 802B configured to abut distal edge 402B of second shell portion 321B, which can be seen in FIG. 7. FIG. 8 further illustrates strain relief element 328 including opposing grooves 823 that provide relief for pins 423 of handle shell portion 321A (FIG. 4A), responsive to lumen 801 being fitted around distal end 610 of hub 360, and responsive to edge 802A interfacing with shell portion 321A, as shown in FIGS. 7 and 9B. With further reference to FIG. 7, lower edge 802B of element 328 terminates surface C that, for example, the fingers of the operator's hand may contact responsive to application of either one of force vectors F-p, F-d as described above by, for example, the operator's thumb. According to some preferred embodiments, strain relief element 328 is formed from a medical grade thermoplastic elastomer, such as Santoprene™ or Medalist®, for example, by injection molding.

FIGS. 9A-D are schematics outlining some construction methods for assembling embodiments of the deflection assembly, for example, for integration into catheter 300 (FIG. 3A).

Figure 9A:
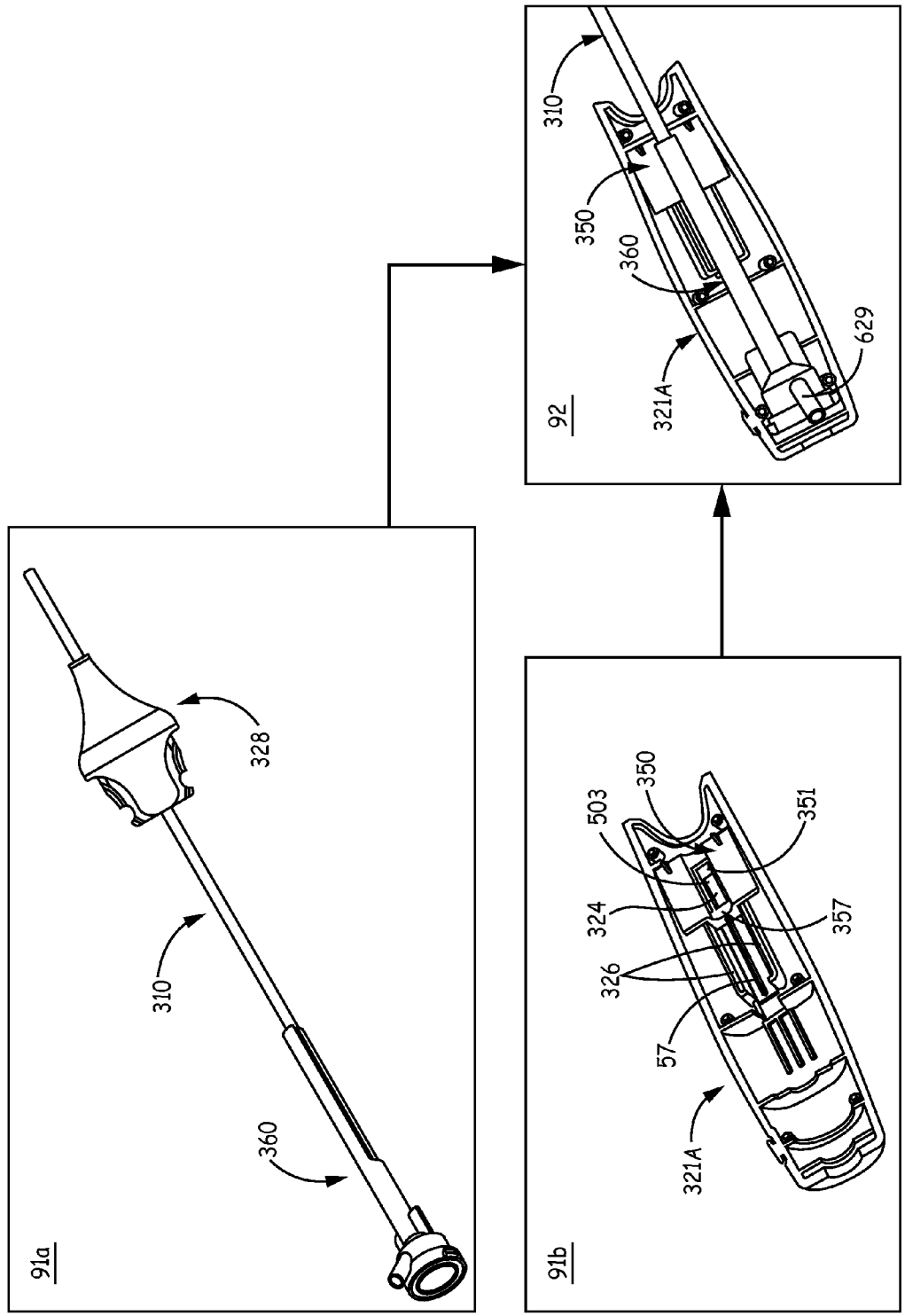
Figure 9D:
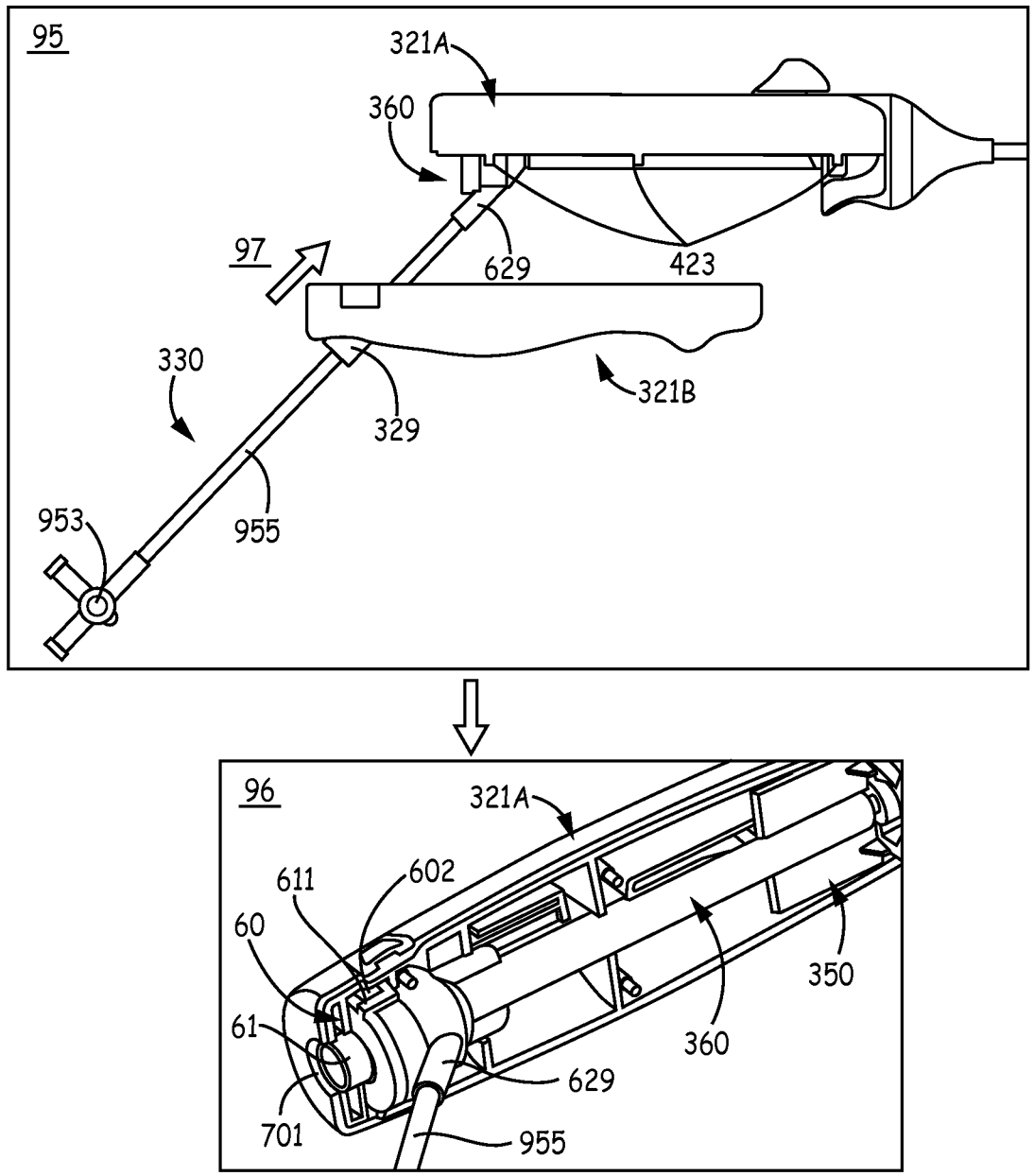

FIG. 9A schematically depicts initial assembly steps 91*a*, 91*b*, in which strain relief element 328 is mounted around catheter shaft 310, either before or after hub 360 is attached to shaft 310, and in which slider component 350 is mounted in first portion 321A of handle shell 321. According to some methods, hub 360 is over-molded onto proximal end 311 of shaft 310, while according to alternate methods, hub 360 is bonded to proximal end 311 of shaft 310. The step 91*b* schematic shows aperture 503 and tail portion 57 of component 350 aligned with handle slot 324, between mating features/rows of teeth 326 of handle shell portion 321A, and open channel 357 of the lower portion of component 350 facing outward from shell portion 321A, so that post 351 extends through slot 324, and so that each engagement feature 356 of the upper portion of component 350 confronts the corresponding mating feature 326 of handle shell portion 321A for the above-described interlocking engagement, which may be seen in part in FIG. 9B. FIG. 9A further illustrates a subsequent assembly step 92, in which hub 360 is mounted in handle shell first portion 321A, being received in open channel 357 of the mounted slider component 350, so that component 350 is in sliding engagement with hub 360, and so that side port 629 of hub 360 extends outward from shell first portion 321A.

FIG. 9B schematically depicts a subsequent step 93 in which the mounted strain relief element 328 is joined to handle shell first portion 321A by interlocking upper edge 802A of element 328 with distal edge 402A of shell first portion 321A. With further reference to FIG. 9B, grooves 823 of strain relief element 328 can be seen providing the above described relief for pins 423 of first shell portion 321A. Furthermore bumper features 55 of slider component 350 are shown abutting a proximal edge of strain relief element 328, for example, to provide a relatively soft stop to the movement of control subassembly 325 in handle slot 324. It should be noted that no secondary bonding processes need be employed in joining element 328 to handle shell 321, according to the illustrated embodiment.

FIG. 9C schematically depicts a subsequent step 94 in which the proximal end of pull wire 315 is secured to post 351 of slider component 350. According to some methods, a proximal end of pull wire 315 extends out from a lumen of shaft 310 when the attached hub 316 was mounted in shell portion 321A, per step 92, so that the proximal end of pull wire 315 was simultaneously inserted through aperture 503 of component 350. But according to some alternate methods, pull wire 315 can be advanced, from either end thereof, through aperture 503 and the pull wire lumen of shaft 310, during step 94. In any case, according to some preferred methods, the proximal end of pull wire 315 is wrapped around and between pillars 351-a, 351-b and then button member 322 is fitted around pillars 351-a, 351-b to complete the securing of pull wire 315 to the mounted slider component 350, per step 94. As was described above, button member 322 preferably includes legs 632 that are inserted through slot 324 and snap fitted within aperture 503 of the mounted slider component 350. With further reference to FIG. 9C, tail portion 57 extends along slot 324 to provide a cosmetic cover over an interior of handle shell 321.

FIG. 9D is a schematic depiction of subsequent steps 95, 96, 97 that complete the assembly of the deflection assembly, according to some methods. In step 95 a flush tube 955 of flushing assembly 330 is attached to hub side port 629, for example, by adhesive bonding, and then threaded through side port 329 of handle shell second portion 321B, prior to attaching a stopcock 953 to a free end of tube 955, for example, by adhesive bonding; or stopcock 953 may be attached to tube 955 prior to threading tube 955 through handle side port 329, from an opposite direction, and then attaching tube 955 to side port 629. According to some alternate methods, hub 360 may be over-molded onto flush tube 955 so that tube 955 is already attached to hub 360 responsive to hub 360 being mounted in handle shell first portion 321A at step 92 (FIG. 9A). FIG. 9D shows, in subsequent step 96, valve subassembly 60 mounted to the proximal opening of hub 360, with valve member 64 (FIG. 6) being press fit within the proximal opening of hub 360, and with valve cap 61 fitting within proximal opening 701 of handle shell 321, having flap members 611 interlocking with laterally protruding features 602 of hub 360. The assembly of subassembly 60 together with hub 360 preferably takes place in subsequent step 96 to prevent possible silicone contamination of flush tube 955 bonding site(s) from a silicone lubrication applied to silicone rubber valve member 64. According to the illustrated embodiment, step 96 need not include any bonding of subassembly 60. Finally, in step 97 (designated with double-line arrow alongside handle shell portion 321B), handle shell portions 321A, 321B are pressed together such that each pin 423 of first portion 321A mates in a press fit with the corresponding receptacle 420 of second portion 321B (FIGS. 4A-B), and handle shell 321 surrounds hub 360, valve subassembly 60, and a majority of control member subassembly 325, for example, as illustrated in FIG. 3A. According to the illustrated embodiment, step 97 need not include any bonding.

In the foregoing detailed description, the invention has been described with reference to specific embodiments. However, it may be appreciated that various modifications and changes can be made without departing from the scope of the invention as set forth in the appended claims.

The invention claimed is:

1. A deflection assembly for a catheter comprising:
an elongate pull wire extending from a proximal end thereof to a distal end thereof;
a handle comprising a shell, first and second rows of teeth, and a railway, the shell having an outer surface, an inner surface, and a slot formed through the shell, the slot having opposing first and second sides and proximal and distal ends that define a length of the slot, the length of the slot extending along a longitudinal axis of the handle, the rows of teeth protruding from the inner surface of the shell, the first row extending alongside the first side of the slot, and the second row extending alongside the second side of the slot, and the railway protruding out from the inner surface of the shell, opposite the slot and toward the slot; and
a control member subassembly comprising a post, to which the proximal end of the pull wire is secured, first and second engagement features, an elastically deformable support, and an operator interface coupled to the post, the operator interface being located adjacent the outer surface of the shell, the post being located in between the first and second engagement features and extending through the slot of the shell, each of the first and second engagement features confronting a corresponding row of the first and second rows of teeth of the handle for interlocking engagement therewith, and the elastically deformable support resting on the railway of the handle; and
wherein, responsive to the elastically deformable support of the control member subassembly being un-deformed, each of the first and second engagement features of the control member subassembly interlock with the corresponding row of the first and second rows of teeth, thereby preventing movement of the control member subassembly along the length of the handle slot;
responsive to a force vector being applied to the operator interface of the control member subassembly, the elastically deformable support deforms against the railway of the handle so that the first and second engagement features of the control member subassembly move out from the interlocking engagement with the first and second rows of teeth of the handle, and the control member subassembly moves along the length of the handle slot, the force vector having a first component directed generally toward the railway and along a vertical axis that is generally orthogonal to the longitudinal axis, and a second component directed along the longitudinal axis;
the elastically deformable support of the control member subassembly comprises first and second flexible cantilever beam members;
the railway of the handle comprises first and second rails extending along the longitudinal axis of the handle and located on an inner surface of the handle, the first rail supporting the first beam member of the control member subassembly, and the second rail supporting the second beam member; and
the deformation of the elastically deformable support in response to the force vector applied to the operator interface comprises a bending of the beam members.

2. The assembly of claim 1, wherein the first and second rows of teeth and the railway of the handle are integrally formed in the inner surface of the shell.

3. The assembly of claim 1, wherein the handle further comprises a stop member configured to limit the bending of the beam members, the stop member extending along the longitudinal axis and protruding from the inner surface of the shell in between the first and second rails.

4. The assembly of claim 1, wherein:
the post of the control member subassembly comprises a pair of pillars extending side-by-side and through the slot of the handle shell, the proximal end of the pull wire extending therebetween; and the operator interface of the control member subassembly comprises a button member fitted around the pillars to secure the proximal end of the pull wire therebetween.

5. The assembly of claim 1, wherein the post, the first and second engagement features, and the elastically deformable support of the control member subassembly are all integrally formed together in a single-piece slider component.

6. The assembly of claim 5, wherein:
the single-piece slider component of the control member subassembly has an upper portion and a lower portion defined along the vertical axis, the upper portion including the first and second engagement features and the post, the lower portion including the elastically deformable support, and the slider component further including a pair of opposing sidewalls extending along the vertical axis, between the upper portion and the lower portion;
each of the first and second engagement features of the slider component comprise a row of teeth formed in a surface of the upper portion of the component; and
the elastically deformable support of the slider component comprises a pair of opposing flexible cantilever beam members, each beam member protruding laterally out from a corresponding sidewall of the pair of opposing sidewalls of the component.

7. The assembly of claim 6, wherein the single-piece slider component further includes an aperture through which the pull wire extends, the aperture extending between the opposing sidewalls, and along the vertical axis from the upper portion to the lower portion.

8. The assembly of claim 6, further comprising:
a hub extending within the shell of the handle and between the first and second rails thereof, the hub including a tubular sidewall that extends from a proximal end thereof to a distal end thereof, an inner surface of the tubular sidewall defining a lumen of the hub, the lumen of the hub having a proximal opening defined by the proximal end of the sidewall and a distal opening defined by the distal end of the sidewall, and the distal end of the tubular sidewall being configured for coupling to a proximal end of a shaft of the catheter; and
wherein the lower portion of the single-piece slider component further comprises an open channel that extends between the pair of opposing flexible cantilever beam members and along the longitudinal axis of the handle, the open channel receiving the tubular sidewall of the hub in sliding engagement therewith.

9. The assembly of claim 1, further comprising:
a hub extending within the shell of the handle and along the longitudinal axis thereof, the hub including a first sidewall and a second sidewall, the first sidewall defining a lumen of the hub, and the second sidewall defining a side port of the hub, the side port being in fluid communication with the lumen of the hub; and
wherein the first sidewall of the hub has a distal end defining a distal opening of the lumen and being configured for coupling to a proximal end of a shaft of the catheter; and
the shell of the handle further comprises a side port formed therethrough, the side port of the hub extending within the side port of the handle shell.

10. The assembly of claim 9, wherein the control member of the subassembly is slideably engaged with the first sidewall of the hub.

11. The assembly of claim 9, wherein:
the hub further includes a valve subassembly, the first sidewall of the hub having a proximal end defining a proximal opening of the lumen to which the valve subassembly is attached; and
the shell of the handle further comprises a proximal opening formed therethrough, the valve subassembly of the hub being fitted within the proximal opening.

12. A deflection assembly for a catheter comprising:
an elongate pull wire extending from a proximal end thereof to a distal end thereof;
a handle comprising a shell, first and second rows of teeth, and a railway, the shell having an outer surface, an inner surface, and a slot formed through the shell, the slot having opposing first and second sides and proximal and distal ends that define a length of the slot, the length of the slot extending along a longitudinal axis of the handle, the rows of teeth protruding from the inner surface of the shell, the first row extending alongside the first side of the slot, and the second row extending alongside the second side of the slot, and the railway protruding out from the inner surface of the shell, opposite the slot and toward the slot;
a control member subassembly comprising a post, to which the proximal end of the pull wire is secured, first and second engagement features, an elastically deformable support, and an operator interface coupled to the post, the operator interface being located adjacent the outer surface of the shell, the post being located in between the first and second engagement features and extending through the slot of the shell, each of the first and second engagement features confronting a corresponding row of the first and second rows of teeth of the handle for interlocking engagement therewith, and the elastically deformable support resting on the railway of the handle; and
a hub extending within the shell of the handle and along the longitudinal axis thereof, the hub including a first sidewall and a second sidewall, the first sidewall defining a lumen of the hub, and the second sidewall defining a side port of the hub, the side port being in fluid communication with the lumen of the hub; and
wherein the first sidewall of the hub has a distal end defining a distal opening of the lumen, the first sidewall being configured for coupling to a proximal end of a shaft of the catheter;
the control member subassembly is slideably engaged with the first sidewall of the hub;
the shell of the handle further comprises a side port formed therethrough, the side port of the hub extending within the side port of the handle shell;
responsive to the elastically deformable support of the control member subassembly being un-deformed, each of the first and second engagement features of the control member subassembly interlock with the corresponding row of the first and second rows of teeth, thereby preventing movement of the control member subassembly along the length of the handle slot; and
responsive to a force vector being applied to the operator interface of the control member subassembly, the elastically deformable support deforms against the railway of the handle so that the first and second engagement features of the control member subassembly move out from the interlocking engagement with the first and second rows of teeth of the handle, and the control member subassembly moves along the length of the handle slot, the force vector having a first component directed generally toward the railway and along a vertical axis that is generally orthogonal to the longitudinal axis, and a second component directed along the longitudinal axis.

13. The assembly of claim 12, wherein:
the post of the control member subassembly comprises a pair of pillars extending side-by-side and through the slot of the handle shell, the proximal end of the pull wire extending therebetween; and
the operator interface of the control member subassembly comprises a button member fitted around the pillars to secure the proximal end of the pull wire therebetween.

14. The assembly of claim 12, wherein the post, the first and second engagement features, and the elastically deformable support of the control member subassembly are all integrally formed together in a single-piece slider component.

15. The assembly of claim 14, wherein:
the single-piece slider component of the control member subassembly has an upper portion and a lower portion defined along the vertical axis, the upper portion including the first and second engagement features and the post, the lower portion including the elastically deformable support, and the slider component further including a pair of opposing sidewalls extending along the vertical axis, between the upper portion and the lower portion;
each of the first and second engagement features of the slider component comprise a row of teeth formed in a surface of the upper portion of the component; and
the elastically deformable support of the slider component comprises a pair of opposing flexible cantilever beam members, each beam member protruding laterally out from a corresponding sidewall of the pair of opposing sidewalls of the component.

16. The assembly of claim 15, wherein the single-piece slider component further includes an aperture through which the pull wire extends, the aperture extending between the opposing sidewalls, and along the vertical axis from the upper portion to the lower portion.

17. The assembly of claim 15, further comprising:
a hub extending within the shell of the handle and between the first and second rails thereof, the hub including a tubular sidewall that extends from a proximal end thereof to a distal end thereof, an inner surface of the tubular sidewall defining a lumen of the hub, the lumen of the hub having a proximal opening defined by the proximal end of the sidewall and a distal opening defined by the distal end of the sidewall, and the distal end of the tubular sidewall being configured for coupling to a proximal end of a shaft of the catheter; and
wherein the lower portion of the single-piece slider component further comprises an open channel that extends between the pair of opposing flexible cantilever beam members and along the longitudinal axis of the handle, the open channel receiving the tubular sidewall of the hub in sliding engagement therewith.

18. A catheter comprising a deflectable shaft and a shaft deflection assembly, the shaft extending from a proximal, terminal end thereof to a distal end thereof, and the deflection assembly comprising:
a pull wire extending within the shaft and having a proximal end exiting the shaft at the proximal terminal end thereof;
a handle shell coupled to the shaft in proximity to the proximal terminal end of the shaft, the shell having an inner surface and an outer surface and a slot formed therethrough, the shell including a mating feature and a railway, both formed in the inner surface, the mating feature extending alongside the slot and the railway extending opposite the slot;
a hub surrounded by the inner surface of the handle shell, the hub including a tubular sidewall and an aperture formed therethrough from an inner surface thereof to an outer surface thereof, the tubular sidewall extending over a length between a proximal end thereof and a distal end thereof, the inner surface of the tubular sidewall defining a lumen of the hub, the lumen of the hub having a proximal opening defined by the proximal end of the sidewall and a distal opening defined by the distal end of the sidewall, the aperture being located in proximity to the distal end of the tubular sidewall, and the distal end of the sidewall being coupled to the shaft so that the proximal end of the pull wire extends through the aperture of the hub; and
a control member subassembly mounted on the hub for sliding engagement therewith, along the length thereof, the control member subassembly including a post to which the proximal end of the pull wire is secured, an engagement feature, a deformable support, and an operator interface coupled to the post, the operator interface being located adjacent the outer surface of the handle shell, the post extending out from the engagement feature and through the slot of the handle shell, the engagement feature confronting the mating feature of the handle shell for interlocking engagement therewith, and the deformable support resting on the railway of the handle shell; and
wherein, responsive to the elastically deformable support of the control member subassembly being un-deformed, the engagement feature of the control member subassembly interlocks with the mating feature of the handle shell, thereby preventing the control member subassembly from sliding along the length of the hub; and
responsive to a force vector being applied to the operator interface of the control member subassembly, the elastically deformable support deforms against the railway of the handle shell so that the engagement feature of the control member subassembly moves out from the interlocking engagement with the mating feature of the handle shell, and the control member subassembly slides along the hub, the force vector having a first component directed generally toward the railway and along a vertical axis that is generally orthogonal to the length of the hub, and a second component directed along the length of the hub.

19. The catheter of claim 18, wherein:
the elastically deformable support of the control member subassembly of the deflection assembly comprises first and second flexible cantilever beam members;
the railway of the handle shell of the deflection assembly comprises first and second rails extending side-by-side along the length of the hub, the first rail supporting the first beam member of the control member subassembly, and the second rail supporting the second beam member; and
the deformation of the elastically deformable support in response to the force vector applied to the operator interface comprises a bending of the beam members.

20. The catheter of claim 19, wherein the handle shell of the deflection assembly further comprises a stop member configured to limit the bending of the beam members, the stop member protruding from the inner surface of the handle shell in between the first and second rails.

21. The catheter of claim 18, wherein:
the post of the control member subassembly of the deflection assembly comprises a pair of pillars extending side-by-side and through the slot of the handle shell, the proximal end of the pull wire extending therebetween; and
the operator interface of the control member subassembly of the deflection assembly comprises a button member fitted around the pillars to secure the proximal end of the pull wire therebetween.

22. The catheter of claim 18, wherein the post, the engagement feature, and the elastically deformable support of the control member subassembly of the deflection assembly are all integrally formed together in a single-piece slider component.

23. The catheter of claim 22, wherein:
the single-piece slider component of the control member subassembly has a vertical axis along which an upper portion and a lower portion of the component are defined, the vertical axis extending approximately orthogonal to the length of the hub, the upper portion including the engagement feature and the post, the lower portion including the elastically deformable support, and the slider component further including a pair of opposing sidewalls extending along the vertical axis, between the upper portion and the lower portion;
the engagement feature of the slider component comprises first and second rows of teeth formed in a surface of the upper portion of the component, the post being located therebetween; and
the elastically deformable support of the slider component comprises a pair of opposing flexible cantilever beam members, each beam member protruding laterally out from a corresponding sidewall of the pair of opposing sidewalls of the component.

24. The catheter of claim 23, wherein the single-piece slider component of the control member subassembly further includes an aperture through which the pull wire extends, the aperture extending between the opposing sidewalls, and along the vertical axis from the upper portion to the lower portion.

* * * * *